Oct. 8, 1957 H. C. SWIM Plant Pat. 1,648
ROSE PLANT
Filed Sept. 26, 1956
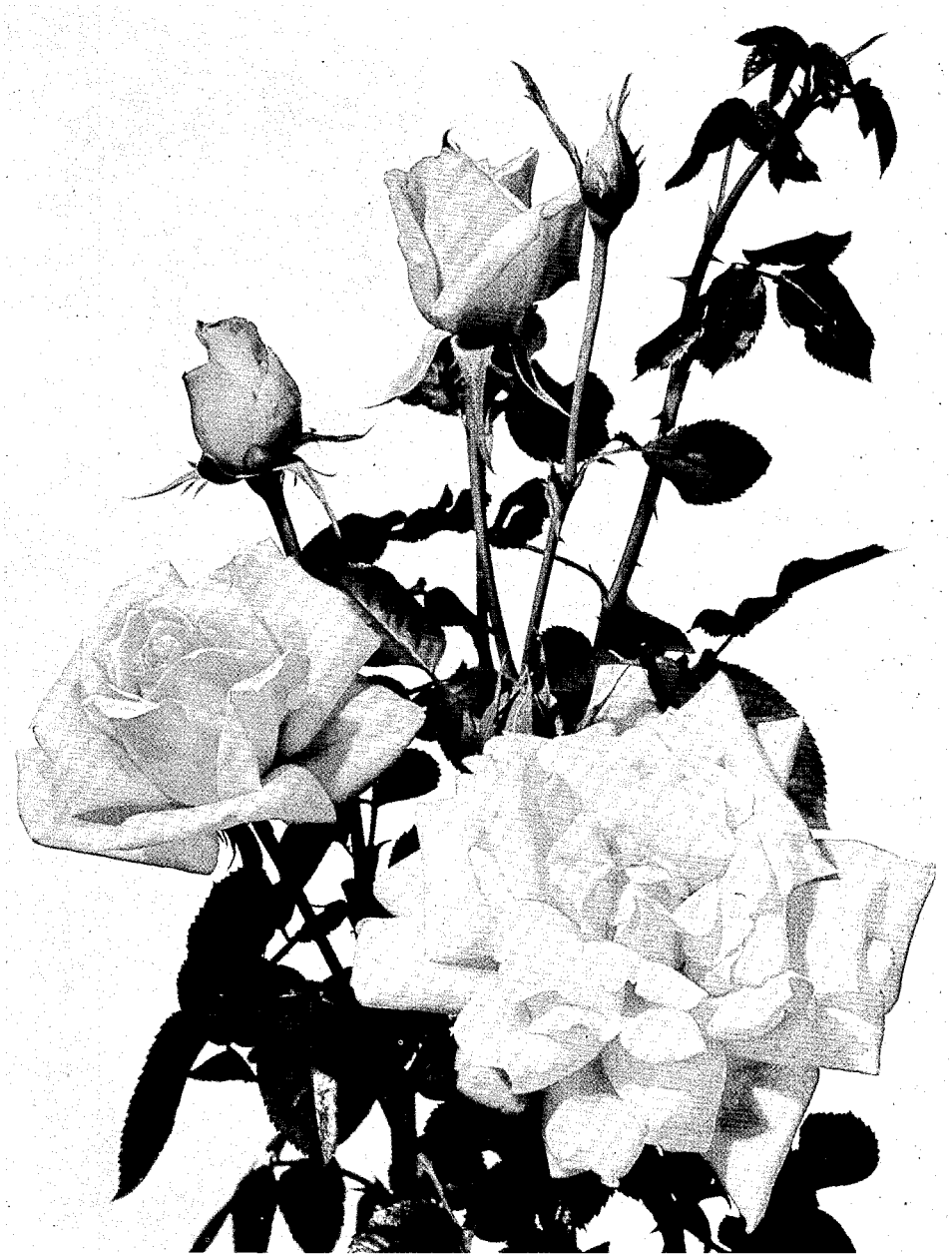
Inventor.
H. C. Swim
By: Robb & Robb
Attorneys United States Patent Office Plant Pat. 1,648
Patented Oct. 8, 1957

1,648

ROSE PLANT

Herbert C. Swim, Ontario, Calif., assignor to Armstrong Nurseries, Inc., Ontario, Calif., a corporation of California Application September 26, 1956, Serial No. 612,345

1 Claim. (Cl. 47—61)

The present invention relates to a new and distinct variety of rose plant of the hybrid tea class, which was originated by me by crossing the variety "Charlotte Armstrong" (Plant Patent No. 455) with an unnamed and unpatented variety, for the purpose of endeavoring to combine the most desirable characteristics of these two varieties.

The variety "Charlotte Armstrong" was used as the seed parent, whereas the unnamed variety was used as the pollen parent, the latter variety having been selected because of its characteristic floribunda type, vigorous and upright habits of plant growth, cluster flowers, with each flower averaging about 3 inches in diameter, and the flowers being double and of a scarlet-orange color.

As the result of the aforementioned breeding, I have produced a new rose variety which is definitely differentiated from its parents, as well as from all other varieties of which I am aware, as evidenced by the following unique combination of predominant features:

(1) A vigorous and spreading plant habit;

(2) Graceful, urn-shaped buds and high-centered flowers approaching those of the parent variety "Charlotte Armstrong";

(3) A flower size approaching that of "Charlotte Armstrong";

(4) Better than average petal substance, with attendant long-lasting qualities of the flowers; and (5) A distinctive orange-scarlet flower color somewhat similar to that of the variety "Montezuma" (Plant Patent No. 1,383), but generally being somewhat darker than that variety.

In comparison with its seed parent "Charlotte Armstrong," the flowers of the new variety are scarlet-orange in color, whereas those of this parent are from blood-red to cerise in color; the petal substance of the new variety is greater than that of this parent; and the growth habit of the plant is spreading, whereas that of this parent is more upright.

As compared with its unnamed pollen parent, the new variety bears its flowers usually from 3 to 4 flowers per stem, but often singly, whereas the pollen parent bears its flowers in relatively large clusters; the flowers of the new variety are substantially larger in size than those of the pollen parent; and the new variety is spreading in its habit of growth, while the pollen parent is upright in habit.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Charlotte Armstrong."

*Pollen parent.*—An unnamed variety.

Propagation: Holds its distinguishing characteristics through succeeding propagations by budding.

*Flower*

Locality where grown and observed: Ontario, California.

Flowers borne: Sometimes singly, but usually 3 or 4 to the stem; on strong stems of from short to medium length.

Quantity of bloom: Free, outdoors.

Continuity: Nearly continuous during growing season.

Fragrance: Moderate. Nature—from tea to spicy.

Bud:

*Peduncle.*—Average length; average caliper; erect; smooth; with some gland-tipped cilia. Color—between Courge Green, Plate XVII (Ridgway) and Biscay Green, Plate XVII (Ridgway), but sometimes lightly overlaid with near Deep Corinthian Red, Plate XXVII (Ridgway) on side exposed to the sun.

*Before calyx breaks.*—Size—medium. Form—medium length; ovoid; with foliaceous appendages; some gland-tipped cilia on the surface of the bud; usually with much-cut foliaceous parts extending beyond the tip of the bud equal to ¼ or more of its length.

*As calyx breaks.*—Color—between Current Red, Plate 821/1, p. 167 (Wilson) and Cardinal Red, Plate 822/1, p. 168 (Wilson).

*Sepals.*—Inner surface with fine, woolly tomentum; margins of alternate sepals lined with fine, woolly tomentum; others lined with stipitate glands and few hairs.

*As first petal opens.*—Size—average. Form—from medium length to long; from pointed to urn-shaped. Color: outside—between Carmine, Plate 21, p. 21 (Wilson) and Crimson, Plate 22, p. 22 (Wilson); inside—between Scarlet, Plate 19, p. 19 (Wilson) and Geranium Lake, Plate 20, p. 20 (Wilson).

*Opening.*—Opens up well; is not retarded from opening by cold, hot, wet or dry weather.

Bloom:

*Size (when fully open).*—Average; from 4 inches to 4½ inches.

*Petalage.*—Double; from 22 to 28 petals, plus 3 to 6 petaloids; arranged regularly.

*Form.*—High-centered at first, but becoming open to cupped later; petals being at first cupped, with lateral margins of outer petals reflexed ½ or more of petal length and lateral margins of inner petal reflexed from ¼ to ½ of petal length, and with apex of outer petals sometimes reflexed to ½ of petal length; becoming flat-cupped later at maturity, with lateral margins of petals reflexed from ½ of petal length to entire length of the petal, and with apex often reflexed from ¼ to ½, or sometimes more, of petal length.

Petals:

*Texture.*—Thick; with inside velvety and outside from shiny to satiny.

*Shape.*—Outside—broadly obovate, with apex flat and rarely with one or two notches. Intermediate—obovate, with apex from rounded to flat, and rarely with one or two notches. Inside—narrowly obovate; irregular; with apex rounded, and with one or two notches.

This description of a newly opened flower was made from a rose grown outdoors in the month of September, at Ontario, California:

*Color.*—Outer petal: outside surface—between Carmine, Plate 21, p. 21 (Wilson) and Crimson, Plate 22, p. 22 (Wilson), with small area at base of petal near attachment near Lemon Yellow, Plate 4/3, p. 4 (Wilson); inside surface—between Scarlet, Plate 19/1, p. 19 (Wilson) and Geranium Lake, Plate 20/1, p. 20 (Wilson), with small area at base of petal near attachment near Lemon Yellow, Plate 4/3, p. 4 (Wilson). Intermediate petal: outside surface—between Geranium Lake, Plate 20/1, p. 20 (Wilson) and Carmine, Plate 21, p. 21 (Wilson), with small area at base of petal near attachment near Lemon Yellow, Plate 4/3, p. 4 (Wilson); inside surface—near Scarlet, Plate 19, p. 19 (Wilson), with small area at base of petal near attachment near Lemon Yellow, Plate 4/3, p. 4 (Wilson). Inner petal: outside surface—between Geranium Lake, Plate 20/1, p. 20 (Wilson) and Carmine, Plate 21, p. 21 (Wilson), with small area at base of petal near attachment near Lemon Yellow, Plate 4/3, p. 4 (Wilson); inside surface—near Scarlet, Plate 19, p. 19 (Wilson), with small area at base of petal near attachment near Lemon Yellow, Plate 4/3, p. 4 (Wilson).

This description was made from a rose that was open for 3 days outdoors in the month of September, at Ontario, California:

*Color.*—Outer petal: outside surface—between Carmine, Plate 21/1, p. 21 (Wilson) and Crimson, Plate 22/1, p. 22 (Wilson), with small area at base of petal near attachment near Aureolin, Plate 3/3, p. 3 (Wilson); inside surface—near Geranium Lake, Plate 20/1, p. 20 (Wilson), marked somewhat with near Carmine, Plate 21/1, p. 21 (Wilson). Inner petal: outside surface—between Carmine, Plate 21/1, p. 21 (Wilson) and Crimson, Plate 22/1, p. 22 (Wilson), with small area at base of petal near attachment near Aureolin, Plate 3/3, p. 3 (Wilson); Inside surface—near Geranium Lake, Plate 20/1, p. 20 (Wilson), marked somewhat with near Carmine, Plate 21/1, p. 21 (Wilson).

*General color effect.*—Newly opened flower—between Scarlet, Plate 19, p. 19 (Wilson) and Geranium Lake, Plate 20, p. 20 (Wilson). 3-days open—near Geranium Lake, Plate 20/1, p. 20 (Wilson).

*Behavior.*—Drop off cleanly; not particularly affected by cold, hot, wet or dry weather.

*Flower longevity.*—On bush in garden—4 or 5 days in September. Cut roses grown outdoors and kept at living-room temperatures—5 or 6 days in September.

*Reproductive organs*

Stamens: From average number to many; arranged regularly about pistils.

Filaments: Medium length; from 7 to 10 mm. in length; most with anthers. Color—upper ¾, near Crimson, Plate 22/2, p. 22 (Wilson); lower ¼ near Dresden Yellow, Plate 64/3, p. 64 (Wilson).

Anthers: Small; all open approximately at once. Color: upper side—margins near Cadmium Orange, Plate 8/2, p. 8 (Wilson), with remainder near Empire Yellow, Plate 603/3, p. 66 (Wilson); under side—margins near Cadmium Orange, Plate 8/2, p. 8 (Wilson), with remainder near Empire Yellow, Plate 603/3, p. 66 (Wilson).

Pollen: Moderate. Color—near Saffron Yellow, Plate 7/2, p. 7 (Wilson).

Pistils: Many; approximately 130 in number.

Styles: Moderately even; from short to average length; from 6 to 8 mm. in length; average caliper; bunched. Color—upper half near Current Red, Plate 821/2, p. 167 (Wilson), with lower half near Uranium Green, Plate 63/3, p. 63 (Wilson).

Stigma: Color—between Empire Yellow, Plate 603/3, p. 66 (Wilson) and Straw Yellow, Plate 604/3, p. 67 (Wilson).

Ovaries: Most enclosed in calyx, but some protruding from calyx.

Hips: Average length; globular; smooth; walls thick and fleshy. Color (⅔ mature)—between Yellowish Citrine, Plate XVI (Ridgway) and Courge Green, Plate XVII (Ridgway).

Sepals: Permanent; medium length; recurved. Color: inside—between Biscay Green, Plate XVII (Ridgway) and Bice Green, Plate XVII (Ridgway), overlaid with near Neutral Red, Plate XXXVIII (Ridgway); masked by white woolly tomentum; outside—between light Elm Green, Plate XVII (Ridgway) and Bice Green, Plate XVII (Ridgway).

Seeds: Average number; 5 to 11 in number; from medium size to large.

*Plant*

Foliage:

*Leaves.*—Compound of usually 5 to 7 leaflets; normal abundance; medium size; leathery; semi-glossy.

*Leaflets.*—Shape—ovoid, with apex acute. Base—round. Margin—doubly serrate. Color: mature—upper surface—between Forest Green, Plate XVII (Ridgway) and Dark Dull Yellow Green, Plate XXXII (Ridgway); under surface—near Light Elm Green, Plate XVII (Ridgway). Young—upper surface—between Dark Corinthian Purple, Plate XXXVIII (Ridgway) and Neutral Red, Plate XXXVIII (Ridgway); under surface—near Corinthian Purple, Plate XXXVIII (Ridgway).

*Rachis (the supporting stem of the compound leaf).*—From slight to average size. Upper side—grooved; with many stipitate glands on edges. Under side—with stipitate glands and from 3 to 5 prickles.

*Stipules.*—Medium length; wide; with medium length points turning out at an angle of about 45°.

*Disease resistance.*—Average resistance to mildew as compared with other varieties grown under comparable cultural conditions at Ontario, California.

Growth:

*Habit.*—Spreading; moderately branched; bushy.

*Growth.*—Vigorous.

*Canes.*—From medium caliper to heavy.

*Main stems.*—Color—near Oil Green, Plate V (Ridgway). Large prickles—many; medium length; hooked downward; with long, narrow base; color—between Pecan Brown, Plate XXVIII (Ridgway) and Mikado Brown, Plate XXIX (Ridgway). Small prickles—few; color—Between Pecan Brown, Plate XXVIII (Ridgway) and Mikado Brown, Plate XXIX (Ridgway). Hairs—none.

*Branches.*—Color—between Light Elm Green, Plate XVII (Ridgway) and Bice Green, Plate XVII (Ridgway). Large prickles—many; medium length; hooked downward; with long, narrow base; color—between Pale Viridine Yellow, Plate V (Ridgway) and Light Yellow Green, Plate VI (Ridgway). Small prickles—from several to many; color—between Pale Viridine Yellow, Plate V (Ridgway) and Light Yellow Green, Plate VI (Ridgway). Hairs—none.

*New shoots.*—Color—between Courge Green, Plate XVII (Ridgway) and Biscay Green, Plate XVII (Ridgway), overlaid somewhat with near Corinthian Purple, Plate XXXVIII (Ridgway). Large prickles—several; medium length; hooked downward; with long, narrow base; color—between Vernonia Purple, Plate XXXVIII (Ridgway) and Deep Hellebore Red, Plate XXXVIII (Ridgway). Small prickles—few; color—near Vernonia Purple, Plate XXXVIII (Ridgway). Hairs—none.

I claim:

A new and distinct variety of rose plant of the hybrid tea class, substantially as herein shown and described, characterized particularly as to novelty by its vigorous and spreading habit of plant growth, graceful, urn-shaped buds and high-centered flowers, good flower size, good petal substance and attendant long-lasting qualities of the flowers, and the distinctive orange-scarlet general color tonality of the flowers.

No references cited.